United States Patent
Jacobs et al.

(10) Patent No.: US 8,317,700 B2
(45) Date of Patent: Nov. 27, 2012

(54) METHODS AND DEVICES FOR NON-INVASIVE ANALYTE MEASUREMENT

(75) Inventors: Peter G. Jacobs, Portland, OR (US);
Dawn Konrad-Martin, Portland, OR (US); Eric Wan, Hillsboro, OR (US)

(73) Assignees: The United States of America as represented by the Department of Veterans Affairs, Washington, DC (US); Oregon Health & Science University, Portland, OR (US)

(*) Notice: Subject to any disclaimer, the term of this patent is extended or adjusted under 35 U.S.C. 154(b) by 360 days.

(21) Appl. No.: 12/294,558

(22) PCT Filed: Apr. 11, 2007

(86) PCT No.: PCT/US2007/066378
§ 371 (c)(1),
(2), (4) Date: Jun. 11, 2009

(87) PCT Pub. No.: WO2007/121209
PCT Pub. Date: Oct. 25, 2007

(65) Prior Publication Data
US 2009/0306490 A1    Dec. 10, 2009

Related U.S. Application Data

(60) Provisional application No. 60/791,059, filed on Apr. 11, 2006.

(51) Int. Cl.
*A61B 5/00* (2006.01)

(52) U.S. Cl. .................................. 600/365; 600/309
(58) Field of Classification Search ............... 600/365, 600/300, 361
See application file for complete search history.

(56) References Cited

U.S. PATENT DOCUMENTS

| | | | |
|---|---|---|---|
| 5,079,421 A | 1/1992 | Knudson et al. | |
| 5,119,819 A * | 6/1992 | Thomas et al. | 600/438 |
| 5,146,091 A | 9/1992 | Knudson et al. | |
| 5,448,992 A * | 9/1995 | Kupershmidt | 600/347 |
| 5,827,181 A * | 10/1998 | Dias et al. | 600/322 |
| 6,113,541 A * | 9/2000 | Dias et al. | 600/301 |
| 6,285,894 B1 | 9/2001 | Oppelt et al. | |
| 6,309,884 B1 | 10/2001 | Cooper et al. | |
| 6,775,564 B1 * | 8/2004 | Peters et al. | 600/316 |
| 6,846,288 B2 * | 1/2005 | Nagar et al. | 600/437 |
| 6,954,662 B2 * | 10/2005 | Freger et al. | 600/316 |
| 7,857,761 B2 * | 12/2010 | Lec et al. | 600/368 |
| 2005/0043602 A1 * | 2/2005 | Freger et al. | 600/365 |
| 2005/0054907 A1 * | 3/2005 | Page et al. | 600/316 |
| 2005/0272990 A1 * | 12/2005 | Ariav et al. | 600/365 |
| 2006/0264717 A1 * | 11/2006 | Pesach et al. | 600/310 |

OTHER PUBLICATIONS

Suckfull, et al., "Changes in Serum Osmolarity Influence the Function of Outer Hair Cells," Acta Otolaryngol (1999) 119:316-321.

(Continued)

*Primary Examiner* — Navin Natnithithadha
(74) *Attorney, Agent, or Firm* — Dann Dorfman Herrell & Skillman; Robert C. Netter, Jr.

(57) ABSTRACT

Methods and compositions for the non-invasive determination of the concentration of an analyte are provided.

19 Claims, 14 Drawing Sheets

OTHER PUBLICATIONS

Sasso, et al., "Cochlear Dysfunction in Type 2 Diabetes: A Complication Independent of Neuropathy and Acute Hyperglycemia," Metabolism (1999) 48:1346-1350.

Dileo, et al., "Cochlear Dysfunction in IDDM Patients with Subclinical Peripheral Neuropathy," Diabetes Care (1997) 20:824-828.

Simoncelli, et al., "Evoked Acoustic Oto-emissions in Patients with Diabetes Mellitus," Ann. Otolaryngol. Chir. Cervicofac. (1993) 110:255-258 (Abstract only).

Hosch, et al., "Otoacoustic Emissions in Diabetic Patients with Normal Hearing," SCweiz. Med. Wochenschr. (2000) 125:83S-85S (Abstract only).

Orts, et al., "The Study of Otoacoustic Emissions in Diabetes Mellitus," Acta Otorrinolaringol Esp. (1998) 49:25-28 (Abstract only).

Lisowska, et al., "Otoacoustic Emissions and Auditory Brain Stem Responses in Insulin Dependent Diabetic Patients," Otolaryngol. Pol. (2002) 56:217-225 (Abstract only).

* cited by examiner

| Region | Number of Points | Percentage |
|---|---|---|
| A | 18 | 48.65% |
| B | 17 | 45.95% |
| C | 2 | 5.41% |
| D | 0 | 0.00% |
| E | 0 | 0.00% |

METHODS AND DEVICES FOR NON-INVASIVE ANALYTE MEASUREMENT

The present application is a §371 application of PCT/US2007/066378 filed Apr. 11 2007 which claims priority under 35 U.S.C. §119(e) to U.S. Provisional Patent Application No. 60/791,059, filed on Apr. 11, 2006. The foregoing applications are incorporated by reference herein.

Pursuant to 35 U.S.C. Section 202(c), it is acknowledged that the United States Government has certain rights in the invention described herein, which was made in part with funds from the National Center for Rehabilitative Auditory Research Grant No. VA RR&D C2659C.

FIELD OF THE INVENTION

The present invention relates to the fields of cochlear and middle ear response to pressure signals and the measurement of blood analytes.

BACKGROUND OF THE INVENTION

Several publications and patent documents are cited throughout the specification in order to describe the state of the art to which this invention pertains. Each of these citations is incorporated herein by reference as though set forth in full.

Studies have shown that persons with type 1 diabetes can significantly reduce the risk of complications associated with the disease by actively monitoring their blood glucose levels (The Diabetes Control and Complications Trial Research Group (1993) New Eng. J. Med., 329:977-986). However, the current method of monitoring blood glucose levels involves painful finger sticks. Many diabetic patients fail to actively manage their glucose for the primary reasons of finger soreness, pain, inconvenience, and fear of needles (Burge, M. R. (2001) Diabetes Care, 24:1502-1503).

Researchers have been searching for ways to noninvasively measure blood glucose in diabetic subjects for years (Sieg et al. (2005) Diabetes Tech. Therap. 7:174-97; Zheng et al. (2000) Diabetes Tech. Therap. 2:17-25). This research has taken one of two approaches: using infrared or near infrared technology to noninvasively obtain optical signatures that are known to correlate with glucose levels; or taking samples of interstitial fluid for analysis. Both of these approaches pose problems, including accuracy issues, skin irritation, and calibration problems (Sieg et al. (2005) Diabetes Tech. Therap. 7:174-97; Zheng et al. (2000) Diabetes Tech. Therap. 2:17-25).

The normal cochlea does not just receive sound. The cochlea also produces low-intensity sounds called otoacoustic emissions (OAEs) that can be evoked using audio stimuli (Brownell, W. E. (1990) Ear and Hearing, 2:82-92). OAEs can provide a noninvasive test of the cochlear mechanical response to acoustic stimuli. OAE tests are already widely used in humans and animals to study cochlear function and the efferent system (Berlin et al. (2002) "Hair Cell Micromechanics and Otoacoustic Emissions" Delmar Learning, Thomason Learning, Inc, Clifton Park, N.Y.).

Suckfull et al. (Acta Oto-Lanryngologica (1999) 119: 316-21) found that OAE amplitudes decreased with an influx of glucose in rabbits under unmasked conditions. Using single-frequency tone bursts to evoke OAEs, Suckfull et al. recorded OAE amplitudes in rabbits while infusing their blood serum with 40% glucose at 10 ml/kg/h and observed a decrease in the evoked OAE amplitudes in response to the elevated glucose level. In contrast, Sasso et al. (Metabolism (1999) 48:1346-1350) examined OAE amplitudes during hyperglycemia for 10 diabetic and 10 nondiabetic human subjects and found no correlation with glucose levels. Notably, the Sasso et al. experiments used clicks to evoke OAEs while Suckfull et al. used pure-tones to evoke them. A click is essentially a representation of all frequencies within the audio spectrum. Neither Sasso et al. nor Suckfull et al. determined a specific correlation between OAE and analyte or glucose concentration or examined the effects of glucose or an analyte on an OAE measured during contralateral or ipsilateral masking.

SUMMARY OF THE INVENTION

In accordance with the present invention, methods are provided for non-invasive analyte measurement and/or assessment of disease state. Specifically, the instant invention employs the measurement of pressure signals related to OAEs and/or the middle ear muscle reflex to determine the concentration of an analyte in the blood of a subject. In a particular embodiment, masked tone-evoked OAEs are used to determine the concentration of the analyte.

Preferably, the measured analyte is associated with a disorder or disease. More preferably, the analyte is glucose and the disease is associated with aberrant glucose levels, such as diabetes.

In accordance with another aspect of the instant invention, a system is provided for non-invasively measuring an analyte. The system comprises a computing device (e.g., computer, handheld computer, or microcontroller), means for producing and recording a pressure signal (e.g., sound card or digital signal processor) with input and output capabilities, means for producing the pressure stimuli (e.g., audio transducer), and means for amplifying and filtering a pressure stimuli.

BRIEF DESCRIPTION OF THE DRAWING

FIG. 3A), the response to a 2000 Hz audio signal (S2; FIG. 3B), the response to both S1 and S2 audio stimuli (FIG. 3C), and the nonlinear distortion product (FIG. 3D). DPOAE is the distortion product otoacoustic emission.

FIG. 5A) while a 50 ms probe tone is presented in FIG. 5B (P2). Both P1 and P2 are presented in the third 1-second interval (P12; FIG. 5C). The nonlinear distortion of the masking effect is shown in FIG. 5D (Pd).

FIG. 8A is a graph of the OAE suppression amplitude observed with changing glucose levels. FIG. 8B is a graph depicting the prediction of glucose levels using a linear regression with the OAE suppression amplitude.

FIG. 9A is a graph showing the OAE suppression amplitude observed with glucose levels. FIG. 9B is a graph depicting OAE suppression latency with glucose levels.

DETAILED DESCRIPTION OF THE INVENTION

Figure 1A:
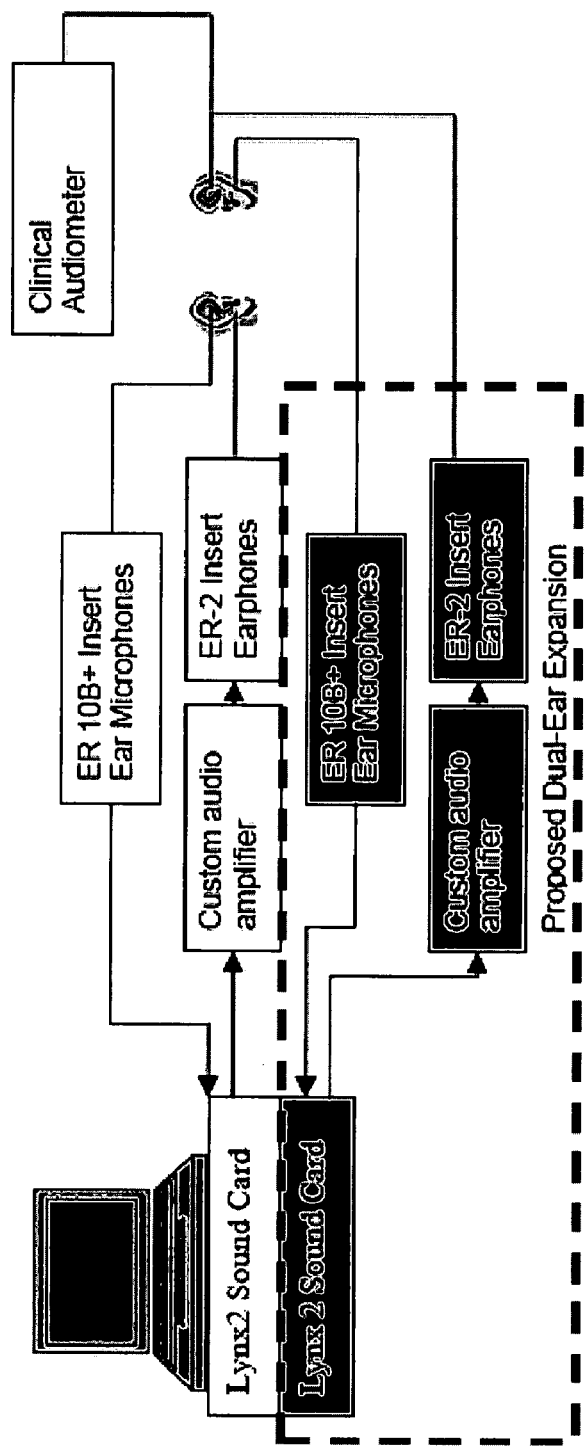
FIG. 1A is a schematic diagram of a noninvasive analyte measurement system used for evoking and recording the OAE.

The present invention relates generally to the non-invasive measurement of at least one analyte. The instant invention provides methods for measuring at least one blood analyte through the use of pressure signals, such as OAEs. Pressure signals are generally longitudinal pressure energy. The pressure signal can be a longitudinal pressure wave (e.g., an audile or inaudible sound wave) or can be a constantly applied pressure. Pressure signals can be used to evoke OAE and/or middle ear responses. While the instant invention is generally exemplified hereinbelow as using OAE, any pressure signal can be used.

As stated hereinabove, OAEs are sounds generated by the cochlea in response to acoustic stimuli and can be recorded by using a small sensitive microphone, which preferably fits snugly inside the ear. OAEs provide a non-invasive test of the cochlear mechanical response.

OAEs can be evoked under either masked or unmasked conditions. Under unmasked conditions, OAEs are evoked by presenting an audio stimulus (e.g., a click, tone, toneburst, or noise signal) to the cochlea using tiny speakers that may fit snugly inside the ear. Under masked conditions, the OAE is evoked in the same way with the exception that a masking audio stimulus (e.g., a click, tone, toneburst, or noise signal) is simultaneously presented contralaterally, ipsilaterally, or both. Contralateral refers to the opposite ear from which the OAE is recorded. Ipsilateral refers to the same ear from which the OAE is recorded.

In a particular embodiment of the instant invention, the acoustic stimuli used to induce the OAEs are masked tones. While certain amplitudes and frequencies are set forth below in the Examples for the tones, the combinations of amplitude, frequency, and masking conditions can be varied. Indeed, such variance of the conditions can lead to the identification of optimal conditions which yield an OAE response which is the most different from the OAE evoked during "no noise" under the same conditions. Optimal conditions may vary between individuals and with individuals over time. Accordingly, recalibration for the conditions may be performed periodically to ensure the precision of the analyte concentration readings. Additionally, conventional methods for measuring the analyte may also be performed to confirm the accuracy of the instant method.

While linear regression models are described below in the Examples, any algorithm that correlates the OAE measurements with the analyte concentration may be employed. For example, linear and nonlinear regression models (e.g., splines or neural networks) may be used to estimate the analyte concentration (Bhandare et al. (1991) Proceedings of the 1991 IEEE Seventeenth Annual Northeast Bioengineering Conference, 249-250; Ghevondian et al. (2001) Proceedings of the 23rd Annual International Conference of the IEEE, Engineering in Medicine and Biology Society, 2:1657-1660).

Multiple linear regression (including, e.g., ridge regression) was used to evaluate whether multiple features, such as amplitude and latency, may be linearly combined to more accurately predict glucose. While multiple linear regression models may be sufficient for predicting glucose using OAE measures, nonlinear models such as artificial neural networks (ANNs) may also be employed. Indeed, ANNs and adaptive learning algorithms have been applied to assessing glucose levels using spectral features from infrared imaging techniques (Long et al. (1990) Anal. Chem., 62:1791-1797; Sandham et al. (1998) Proceedings of the 20th Annual International Conference of the IEEE Engineering in Medicine and Biology Society, 3:1438-1441). ANNs have also been shown to be effective at analyzing otoacoustic emissions to assess sensorineural hearing loss (de Waal et al. (2002) S. Afr. J. Commun. Disord., 49:28-39; Zheng et al (2000) Diabetes Tech. Ther. 2:17-25). Similar techniques may be used to assess glucose levels based on temporal and spectral features from the suppressed and unsuppressed OAEs. For example, multilayer feed-forward neural networks (Haykins, S. (1998) "Neural Networks: A Comprehensive Foundation" Prentice Hall; 2nd edition) may be trained due to their ease of use and proven success in numerous fields, including other otoacoustic emission data analysis applications (de Waal et al. (2002) S. Afr. J. Commun. Disord., 49:28-39; Zheng et al (2000) Diabetes Tech. Ther. 2:17-25). The input vector to the ANN may include, for example, the temporal and spectral features of the OAE response and the stimulus paradigm used to evoke the OAE. Patient-specific information such as age, gender, or even hearing test results and diabetes history may even be included as input to a model or ANN. Furthermore, patient-specific models, while fit using data from an individual patient, may be improved by incorporating information from other patient models using mixed effects models (Laird et al. (1982) Biometrics, 38:963-974). Population based priors derived from mixed effects models may provide effective regularization without the extensive individual subject data requirements of cross-validation.

Both patient-specific and patient-independent models can be generated because of the potential variability between individuals. Patient independent models can be designed using subsets of all the subject data and testing the model on the remaining data using standard techniques, such as a standard V-fold cross-validation technique. The models can also be fit to each test subject individually and then validated using data acquired from the same test subject at a later point in time, e.g., days, weeks, or months later. The determined relationship between OAEs and the concentration of analyte may be referred to as a standard curve. A standard may refer to a sample or set of samples of known concentration used to construct a standard curve.

In a particular embodiment of the instant invention, the analyte being measured is associated with a disease or disorder. Exemplary analytes include, without limitation, alanine aminotransferase, aspartate aminotransferase, albumin, amylase, iron, hemoglobulin, alkaline phosphatase, bilirubin, cholesterol, high density lipoproteins, creatine kinase, creatine kinase isoenzymes, creatinine, glucose, lactate dehydrogenase, lactate dehydrogenase isoenzymes, blood gas (e.g., $O_2$ and $CO_2$), blood pH, calcium, chloride, sodium, magnesium, potassium, urea nitrogen, uric acid, triglycerides, and total protein. In a preferred embodiment, the analyte is glucose. Indeed, the systems and methods of the instant invention may be used by diabetic patients (both type 1 and type 2 diabetics) to monitor their blood glucose levels.

The data provided hereinbelow demonstrates that OAE amplitudes evoked under conditions of contralateral and/or ipsilateral noise masking may correlate more significantly with glucose level than when evoked in the unmasked condition. OAE amplitudes are diminished by activation of efferent neural projections to the cochlea from the brainstem when a competing sound is presented to either the contralateral ear, ipsilateral ear, or both (Hood et al. (1997) ARO Abstracts, 20:167). Glucose has been shown to affect auditory processing and auditory neural pathways, including evoked responses and axonal transmission latencies during the hyperglycemic state (McCrimmon et al. (1997) Neuropsychologia, 35:1547-1553; Rayner et al. (1999) Digest. Dis. Sci., 44:279-285; Russo et al. (1998) Eur. J. Clin. Invest., 29:512-518; Sindrup et al. (1988) Acta Neruol. Scand., 78:141-5). Studies of the auditory brainstem response (ABR) show central conduction time delays in diabetic subjects, changes during insulin-induced hypoglycemia, and during glucose clamp induced hyperglycemia conditions (Bayazit et al. (2000) Auris Nasus Larynx 27:219-222; Bayazit et al. (2000) J. Neurol. Sci., 181:29-32; Deutsch et al. (1983) Electroenceph. Clin. Neurophys., 55:714-71; Lisowska et al. (2001) 0 to 1. Neurot., 22:316-20; Nakamura et al. (1991) Electromyog. Clin. Neurophys., 31:243-9; Sasso et al. (1999) Metabol., 48:1346-1350; Ziegler et al. (1991) Diabet. Med., 8:805-811). An inverse relationship between ABR wave latencies and plasma glucose has also been demonstrated (De Feo et al. (1988) J. Clin. Invest., 82:436-444). Without being bound by theory, it appears that OAEs acquired during contralateral or ipsilateral noise masking may provide a more robust correlation with glucose because the process of masking introduces a neural modulation of the OAE response (Giraud et al. (1995) Brain Res., 705:15-23; Maison et al. (1997) Intl. J. Neurosci., 88:261-72; Scharf et al. (1994) Hearing Res., 75:11-26; Williams et al. (1993) Scand. Audiol., 22:197-203).

Figure 1B:
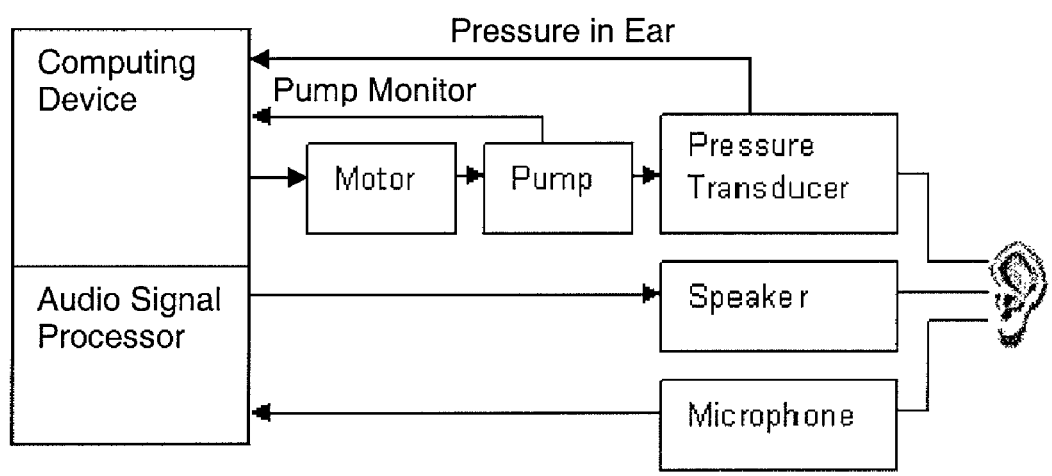
FIG. 1B is a schematic diagram of a noninvasive analyte system used for evoking and recording both an OAE and a MEM reflex response.
Figure 2:
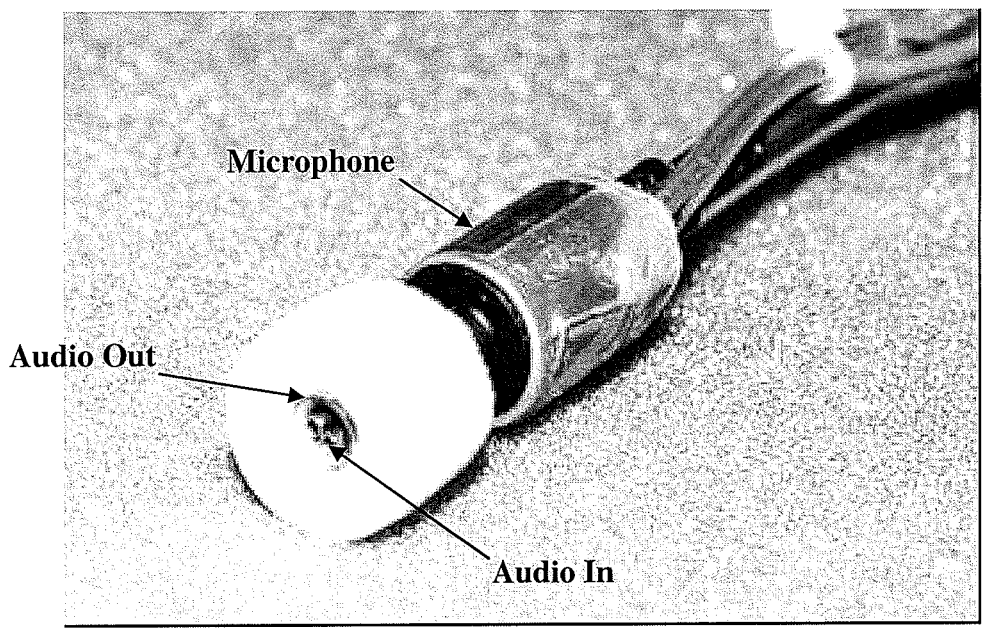
FIG. 2 is a picture of an OAE measurement apparatus identifying the audio in and out ports and the microphone.

In accordance with another aspect of the instant invention, a system is provided for non-invasively measuring an analyte. An exemplary schematic diagram of the system is provided in FIG. 1. The system comprises at least one each of a computing device to handle data acquisition, means for producing and recording a pressure signal (e.g., sound) with input and output capabilities (e.g., analog audio input and output capabilities), means for producing the pressure stimuli, and, optionally, means for amplifying and filtering the pressure stimuli. The system may also comprise software or means for converting the pressure signal information to an output of analyte levels (e.g., glucose levels). The system may also comprise a visual display for the analyte concentration and/or provide a physical print out of the analyte concentration. Exemplary computing devices include, without limitation, a computer, handheld computer, CPU, processor, or microcontroller. Exemplary means for producing and recording pressure signals with input and output capabilities include, without limitation, at least one sound card (e.g., CardDeluxe™ and Lynx2 sound card) or digital signal processor. The system may also comprise at least one audio amplifier to amplify the output of the sound card. The system may comprise an insert earphone (e.g., Etymotic Research ER-2 earphone) and a microphone to record the pressure signals such as OAEs (e.g., ER 10B+ probe microphone). In a particular embodiment, the instant system is contained within a handheld device for convenience and provides a readout of the determined analyte level (e.g., by a visual display, print out, or by transmission to a computer). In another embodiment, the system is contained within a set of headphones. The systems and methods of the instant invention may be used in the home or in clinical settings.

The National Center for Rehabilitative Auditory Research (NCRAR) has developed a desktop software application called AudioTest that is used to present audio stimuli to research test subjects while simultaneously recording psychoacoustic measures from the subjects. To record OAEs, an audio stimulus may be generated through such software, produced by a sound card and delivered through insert earphones coupled to a probe microphone assembly. The OAE is measured by the microphone and then sent to one of the inputs on the sound card where the software acquires and processes the OAE response. Despite the system's sophistication, all hardware components are readily obtainable and the system may be readily customized into a hand-held system for consumer use.

The devices of the instant invention may also be calibrated by the user prior to receiving information about their glucose levels. Calibration may require one using an OAE glucose monitoring device to take one or more finger pricks at certain times during the day so that the device could make an accurate conversion from the OAE measures to a true glucose level. The number of calibration points needed may be determined such that the device yields a clinically acceptable level of accuracy in glucose prediction. The calibration accuracy may be monitored at later times. For example, the calibration may be tested at regular intervals, such as daily, weekly, biweekly, or monthly.

As stated hereinabove, various types of auditory stimuli may be used to evoke the OAE including clicks, tones, and chirps. Clicks provide a wide-band stimulus which causes a large section hair cells located along the basilar membrane within the cochlea to vibrate. A tone is a narrow-band signal that causes a smaller number of hair cells located along the basilar membrane to vibrate. A chirp stimulus represents a sweep of multiple frequencies within a pulse and it therefore causes sub-sections of the hair cells located along the length of the basilar membrane to respond to the stimuli in synchronous order. Chirps have been shown to be effective at improving signal-to-noise ratio especially for people who suffer from hearing impairment (Neumann et al. (1994) Hear Res., 79:17-25).

The instant invention encompasses methods of determining the concentration of an analyte by measuring changes in a characteristic of a measured pressure signal, such as an OAE. The characteristic can be any measurable feature of the signal. Characteristics include, without limitation, amplitude, latency, signal-to-noise ratio, rise time, fall time, frequency, phase, and duration.

There are many ways to suppress an OAE including presenting a noise suppressor contralaterally, ipsilaterally, binaurally and with various temporal patterns and spectral bandwidths. A multi-tone stimulus may also be used to identify suppression due to medial olivocochlear (MOC) and middle ear muscle (MEM) reflexes. Exemplary stimulation parameters are listed in Table 1. Table 1 is not intended to be comprehensive and only gives a sample of the different parameters that can be used.

TABLE 1

Exemplary OAE stimulus parameters

| OAE Measurement Paradigm | Frequency of Probe and Masker | Masker Level [dBSPL] | Probe Level [dBSPL] | Suppression Type |
|---|---|---|---|---|
| DPOAE | Pure Tone (1260 Hz) | 50 | 50 | Ipsilateral |
| TEOAE | Pure Tone (2000 Hz) | 60 | 60 | Contralateral |
| SFOAE | Noise - White | 70 | 70 | Binaural |
| | Noise - Narrow Band | 80 | 80 | None |
| | Narrow band chirp - 630-1890 Hz | | | |
| | Narrow band chirp - 1000-3000 Hz | | | |

The following examples are provided to illustrate various embodiments of the present invention. They are not intended to limit the invention in any way.

EXAMPLE 1

Experiments with Contralateral and Ipsilateral Suppression

The instant studies were conducted at the National Center for Rehabilitative Auditory Research (NCRAR), which currently has two fully-equipped OAE measurement systems located onsite. The systems enable accurate measurements of OAE from either ear with or without contralateral and/or ipsilateral masking.

The purpose of this study was to determine which audio stimulus paradigms may be used to evoke reliable and repeatable OAEs that exhibit efferent feedback suppression in diabetic and nondiabetic subjects.

Various methods for suppressing the OAE using contralateral and ipsilateral noise stimuli were examined.

To measure the subject's OAEs, a double-evoked (2E) measurement technique was used that measures a nonlinear residual (Keefe et al. (1998) J. Acoust. Soc. Amer., 103:3499-508). In this technique, frequency tones are presented to the ear in triplets in one-second increments. The audio stimulus presented in the first one-second interval is typically referred to as a masker while the audio stimulus presented in the next second is referred to as the probe. The masker and the probe are presented simultaneously during the third second of the 3-second triplet stimulus. The cochlear response to the masker may be referred to as P1. The response to the probe may be called P2 and the response to both the masker and probe played simultaneously may be referred to as P12. It has been shown that when the masker and probe are played simultaneously, the OAE response is smaller in amplitude than the sum of the response of the masker and probe played independently. This reduction in amplitude is referred to as the non-linear distortion product of the cochlear response. This non-linear residual distortion product (Pd) of the cochlear response to the audio stimuli can be calculated using equation 1 below. FIGS. 3A-3D provide an example of an OAE measurement taken with this paradigm.

$$Pd = P1 + P2 - P12 \quad [1]$$

Figure 4A:
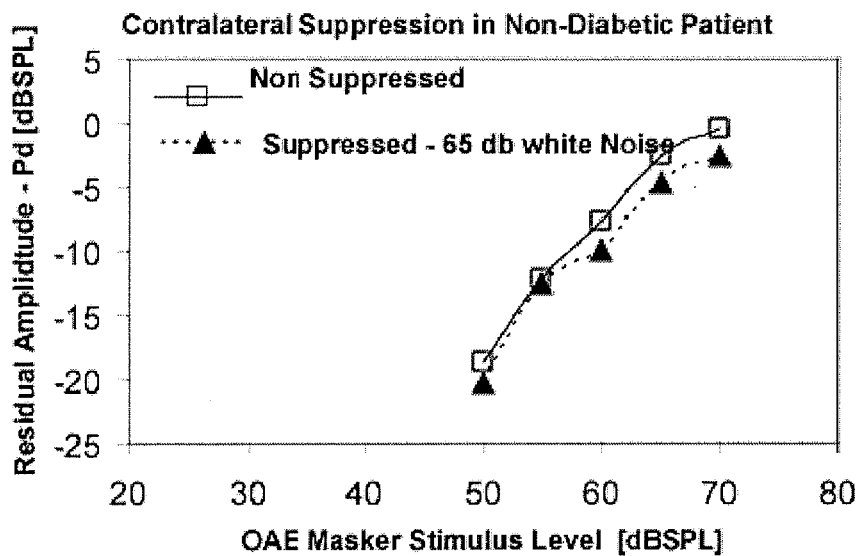
FIGS. 4A and 4B are graphs of the contralateral suppression results for a nondiabetic subject (FIG. 4A) and a diabetic patient (FIG. 4B).
Figure 4B:
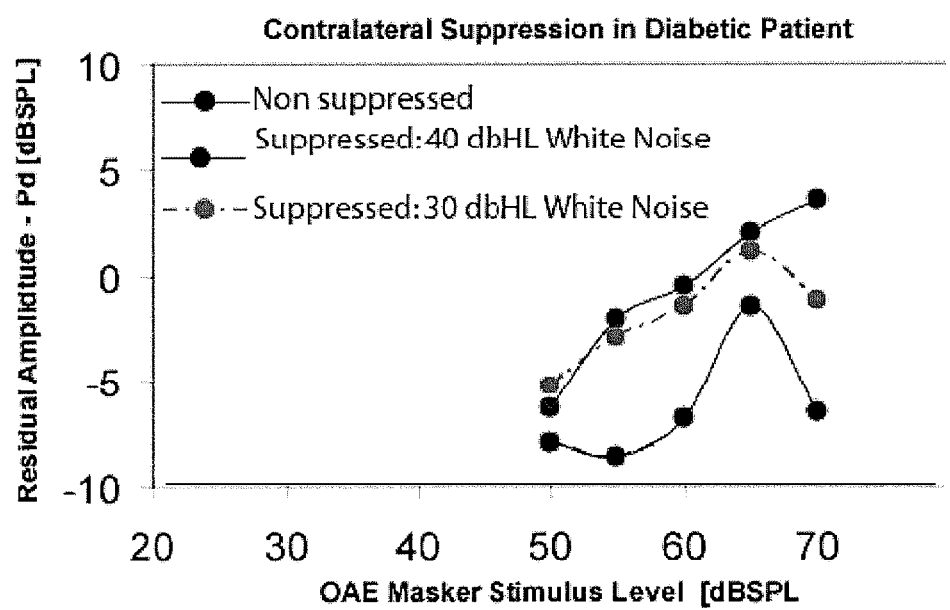
Figure 5:
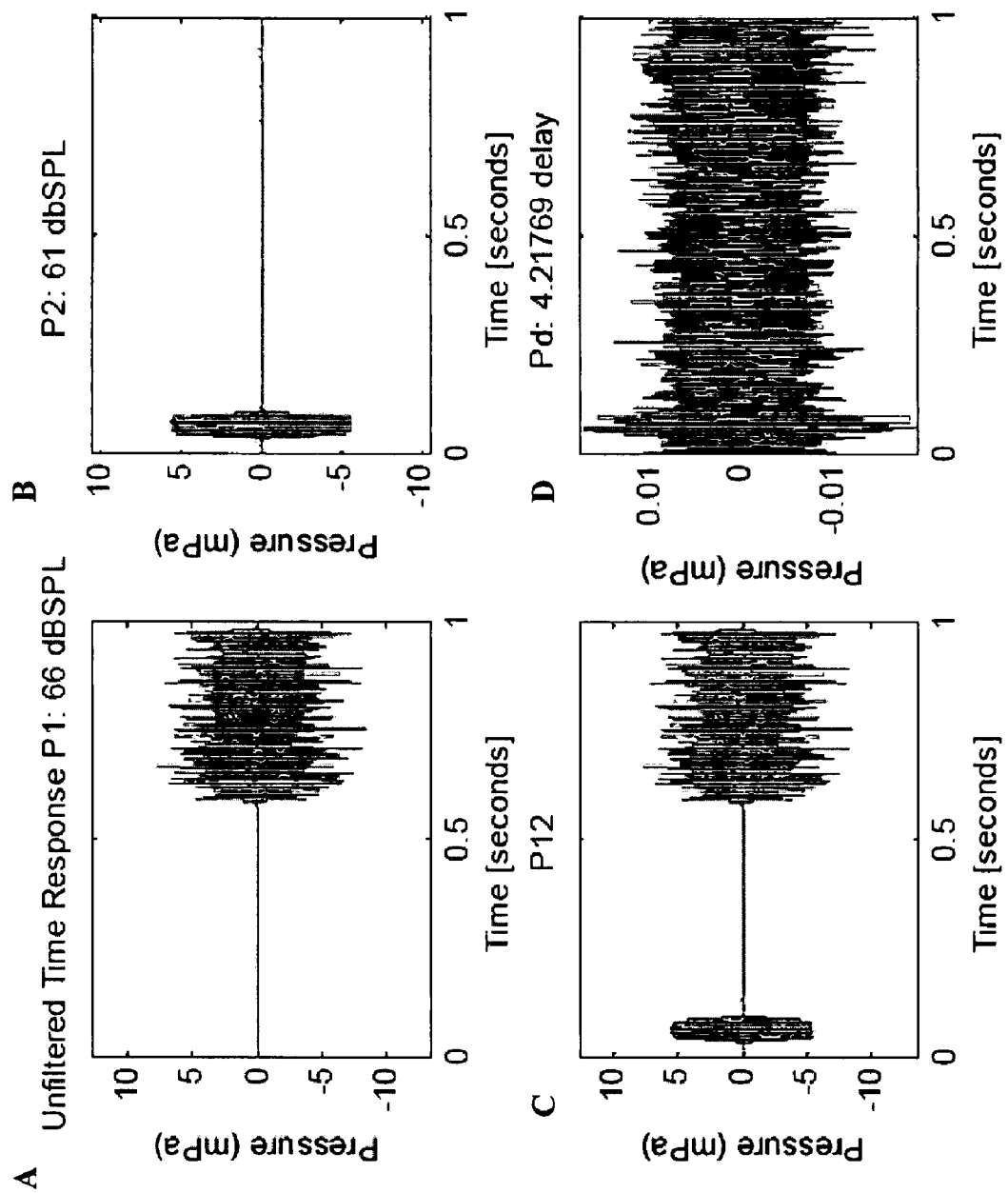
FIGS. 5A-5D are graphs of the forward masking OAE recording in a diabetic patient. A 400 ms noise masker tone is played in the first 1-second interval (P1.

Ten diabetic and two non-diabetic subjects were subsequently tested. To determine the affect of contralateral noise on the OAE, the double-evoked measurement technique described above was used to stimulate the ipsilateral ear while a constant noise signal was presented to the contralateral ear. A contralateral suppression effect was measured in both non-diabetic and diabetic subjects as shown in FIGS. 4A-4B. The suppressed OAE response is lower in amplitude for several masker (P1) stimulus levels (e.g., 55, 60, 65, and 70 dBSPL).

Different stimulus parameters were tested in this study to determine the stimulus parameter values and combinations that would yield a repeatable contralateral suppression effect of the OAE. Amplitude, frequency, and duration of the masker and probe signals were varied as was the level and type of contralateral noise. Both white noise and narrow-band noise centered about the probe frequency were tested as the contralateral suppressor signal. Based on this testing, two stimulus patterns were determined to be preferable for evoking a repeatable contralateral suppression effect. These two combinations are shown in Table 2.

TABLE 2

| | Amplitude | Frequency [Hz] | Duration [ms] |
|---|---|---|---|
| Combination 1 | | | |
| Masker | 66 dBSPL | 1940 | 10 |
| Probe | 51 dBSPL | 2000 | 10 |
| Contralateral Noise | 50 dBHL | White noise | Constant |
| Combination 2 | | | |
| Masker | 76 dBSPL | 1940 | 10 |
| Probe | 61 dBSPL | 2000 | 10 |
| Contralateral Noise | | White noise | Constant |

Both parameter combinations 1 and 2 above were used in the studies below to test contralateral suppression correlation with blood glucose during a glucose tolerance test.

Not all of the diabetic subjects demonstrated a strong contralateral suppression effect. Several of the subjects had low suppression signal-to-noise ratio (SNR) of the OAE response which made it difficult to measure the suppression effect. The suppression SNR is defined as the suppressed OAE residual subtracted from the unsuppressed OAE residual. If no suppression is present, the suppression SNR is zero. Many of the subjects tested had moderate hearing loss (i.e., thresholds above 20 dBHL) and therefore had relatively small OAEs.

The contralateral suppression is expected to be small (several decibels) for normal hearing people. For patients with hearing impairment, the contralateral suppression effect can disappear. To overcome the issue of low suppression SNR, the use of an ipsilateral suppression stimulus paradigm was examined, which resulted in significantly higher SNR of the suppressed OAE response.

Figure 3:
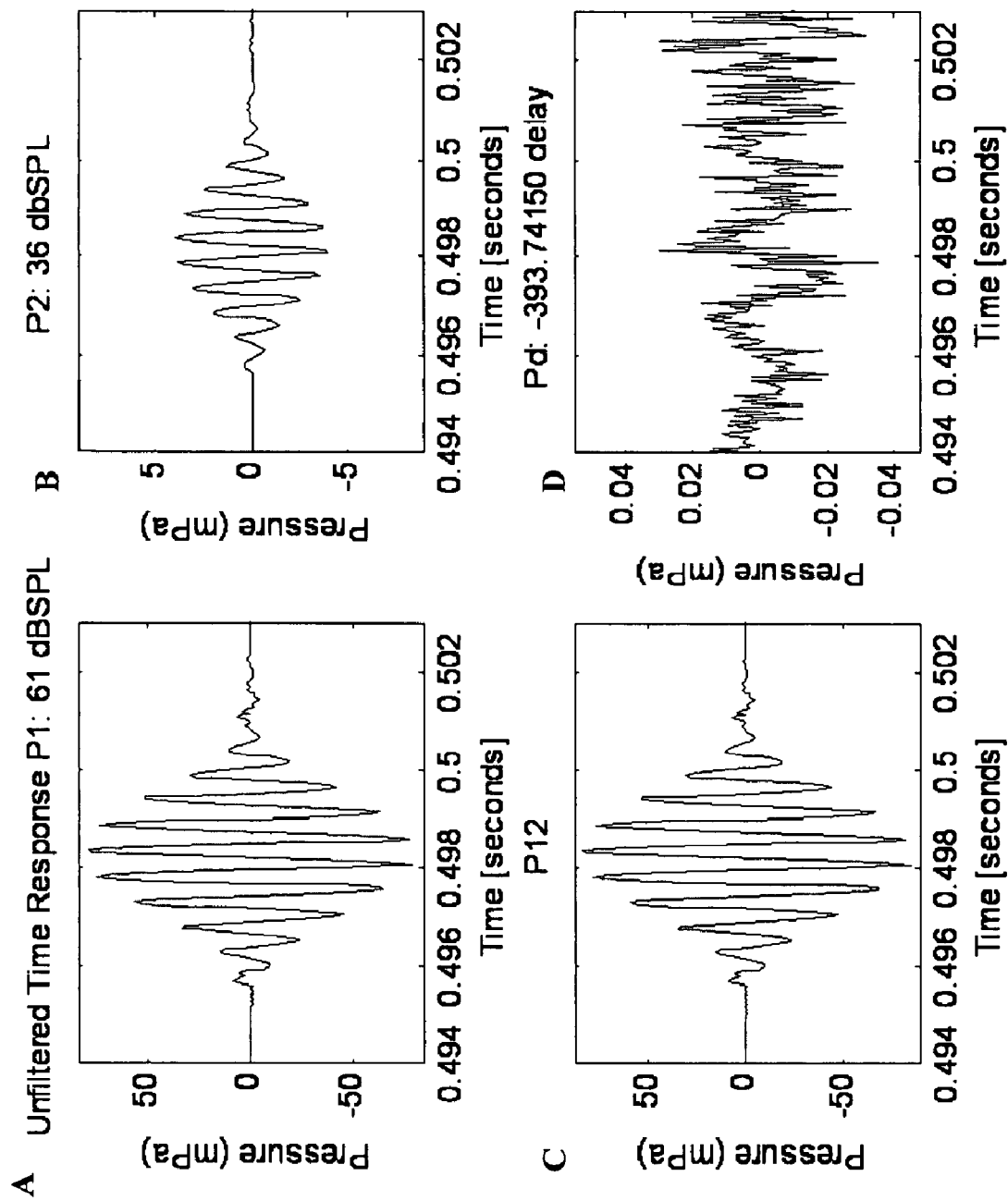
FIGS. 3A-3D are graphs of the response to a 1940 Hz audio stimulus (S1.

In the ipsilateral suppression stimulus paradigm, the double-evoked OAE stimulus method was again used, with a slight difference. In this stimulus paradigm, the masker signal (P1) is presented immediately before the probe signal (P2) in the 3-second stimulus triplet. Recall that in the contralateral stimulus paradigm, the masker and the probe are played at the same time within the 1-second stimulus windows (i.e., at 0.5 seconds as is shown in FIG. 3). By presenting the masker immediately before the probe, the cochlear response to the probe is smaller in amplitude than if the probe was presented without a masker preceding it. This ipsilateral suppression effect is hypothesized to be neural in origin and a result of efferent feedback to the basilar membrane which modulates the OAE response to audio stimuli. It is believed that the masker preceding the probe causes an efferent feedback modulation of the hair cells of the basilar membrane within the cochlea, making the hair cells of the basilar membrane stiffer, and thereby reducing the OAE's response to the probe signal (Liberman M. C. (1992) "Afferent and efferent innervation of the cochlea: stimulus coding and the role of the efferent feedback". Symposium on Neural Mechanisms of the Auditory and Vestibular Systems II, Johns Hopkins University, Baltimore, Md., Dec. 1-2, 1992). The literature suggests the effect of ipsilateral suppression using a forward masker is several times larger than contralateral suppression (Berlin et al. (1995) Hear Res., 87:96-103) and the data presented herewith confirmed this for both diabetic and nondiabetic subjects. A waveform demonstrating the audio stimulus pattern for ipsilateral suppression using a forward masker paradigm is shown in FIGS. 5A-5D.

The masking effect generated using the ipsilateral forward masking stimulus frequency paradigm may be calculated as:

$$Pd = P12 - (P1 + P2) \qquad [2]$$

In equation 1, the masking effect is taking place in P12, when the masker and probe are presented simultaneously. Therefore, (P1+P2) should be larger than P12. In equation 2 using ipsilateral forward-masking, the masking is taking place in P2, since P1 is immediately preceding P2. In P12, the probe is not being preceded by P1. Therefore, P12 should be larger than (P1+P2). Intuitively, if there is no forward masking affect, the amount of OAE suppression (Pd) would be expected to be zero. Indeed, when ipsilateral suppression measurements were taken using a forward masker within a 2 cc coupler artificial ear, no Pd response was observed.

Multiple probe/masker parameter combinations of signal amplitude, frequency, and duration were tested on the diabetic and nondiabetic subjects to determine the stimulus patterns that could evoke a repeatable suppression effect. Based on these tests, the following parameters were preferred for evoking a repeatable ipsilateral suppression effect in the OAE. These parameters were used hereinbelow as stimuli during the glucose tolerance test. These parameters are exemplary and other audio stimuli may be employed.

TABLE 3

|  | Amplitude | Frequency [Hz] | Duration [ms] |
|---|---|---|---|
| Masker | 80 dBSPL | Narrow band noise centered at 1260 Hz | 400 |
| Probe | 80 dBSPL | 1260 | 50 |

The preliminary experiments done with ipsilateral suppression using a forward masker yielded a suppression effect that was several times larger than the suppression effect observed using contralateral suppression. This is in agreement with what has been found in the literature. Further, it may be expected that a binaural suppression paradigm will yield an even larger suppression effect (Berlin et al. (1995) Hear Res., 87:96-103).

EXAMPLE 2

Contralateral Masking During A Glucose Tolerance Test (GTT)

Figure 6A:
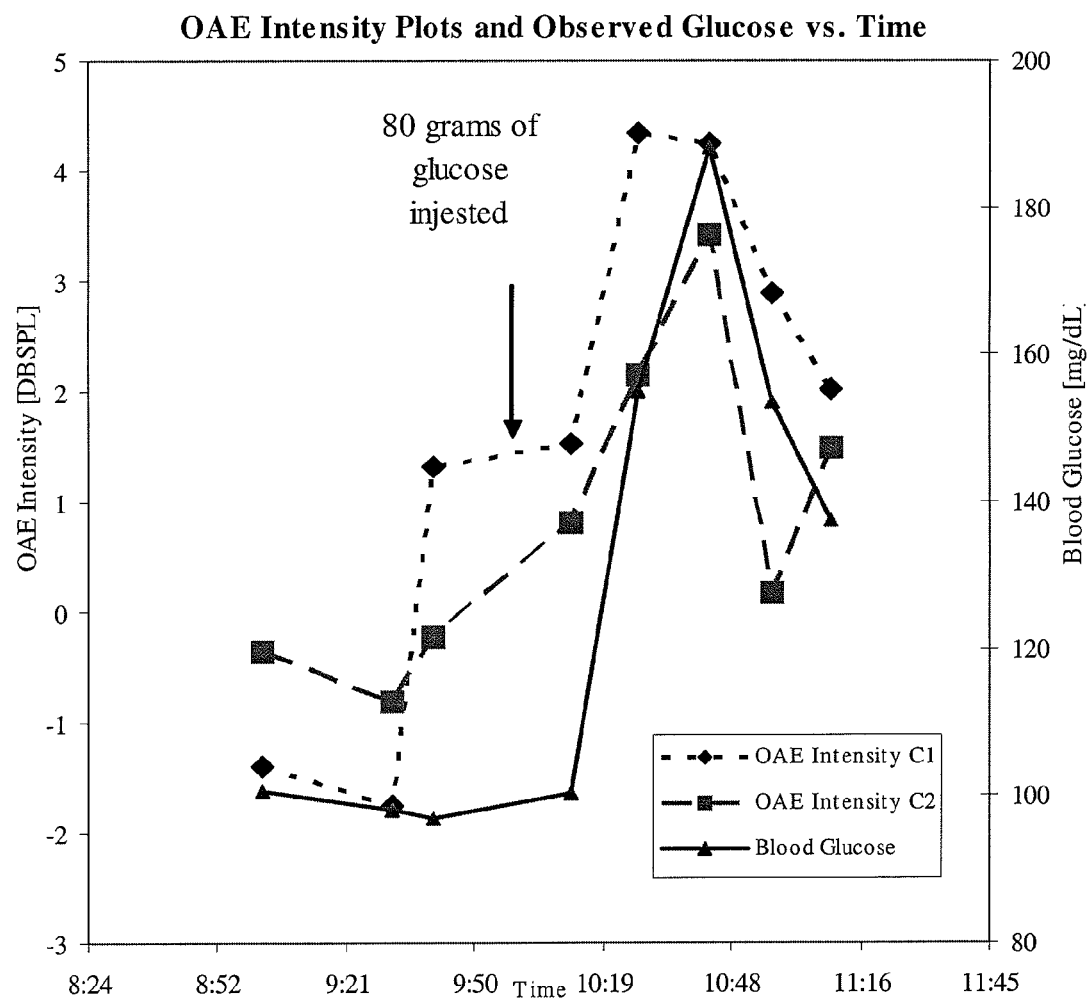
FIG. 6A is a graph of the OAE amplitude recordings evoked during contralateral noise masking taken during a glucose tolerance test. The arrow shows when the subject ingested 80 grams of glucose.

Whether the contralateral suppression of an OAE varied in amplitude and latency during a glucose tolerance test was studied. Gilligan et al. (Diabetes Tech. Ther. (2005) 6:378-86) provides exemplary standard glucose tolerance test protocols. A subject with normal hearing and no history of diabetes fasted overnight for 8 hours prior to testing. Baseline OAE measurements were recorded both with contralateral noise and without. The amplitude, frequency, and duration parameters used for the probe, masker and contralateral audio stimuli were selected based on the studies described above and are listed in Table 2. The sound pressure levels used in the test are well below any levels that would do damage to a patient's hearing during repeated tests. Several baseline glucose readings were recorded using a TheraSense FreeStyle® glucose meter. The subject then consumed 80 grams of glucose in the form of tablets. For the next 1.5 hours, OAE measurements were taken and the subject's blood glucose levels were recorded every 5-10 minutes as the subject's glucose level went high and then dropped low (FIG. 6A). OAEs were recorded alternatively with contralateral noise present and without noise.

Figure 6B:
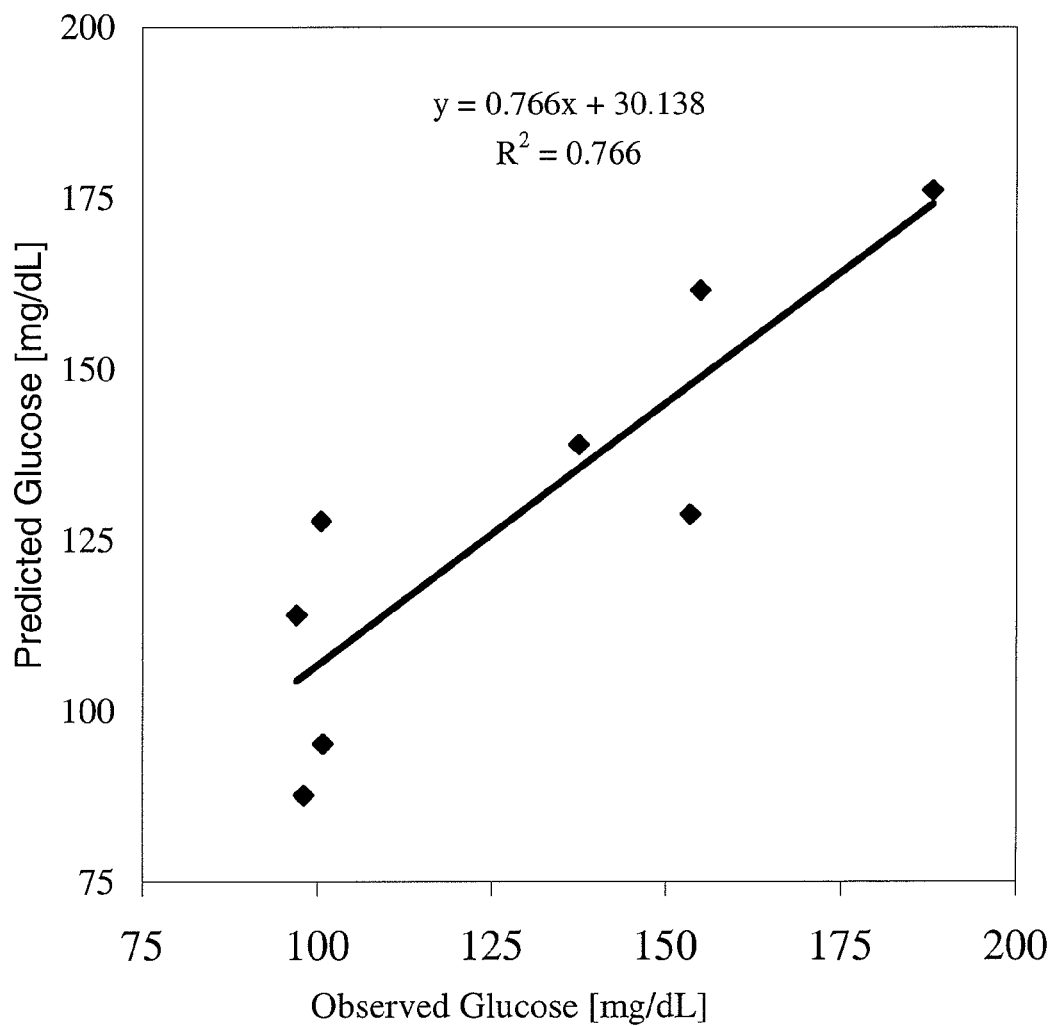
FIG. 6B is a graph representing multiple linear regression using OAE amplitudes during contralateral noise for stimulus combinations listed in Table 2.
Figure 7:
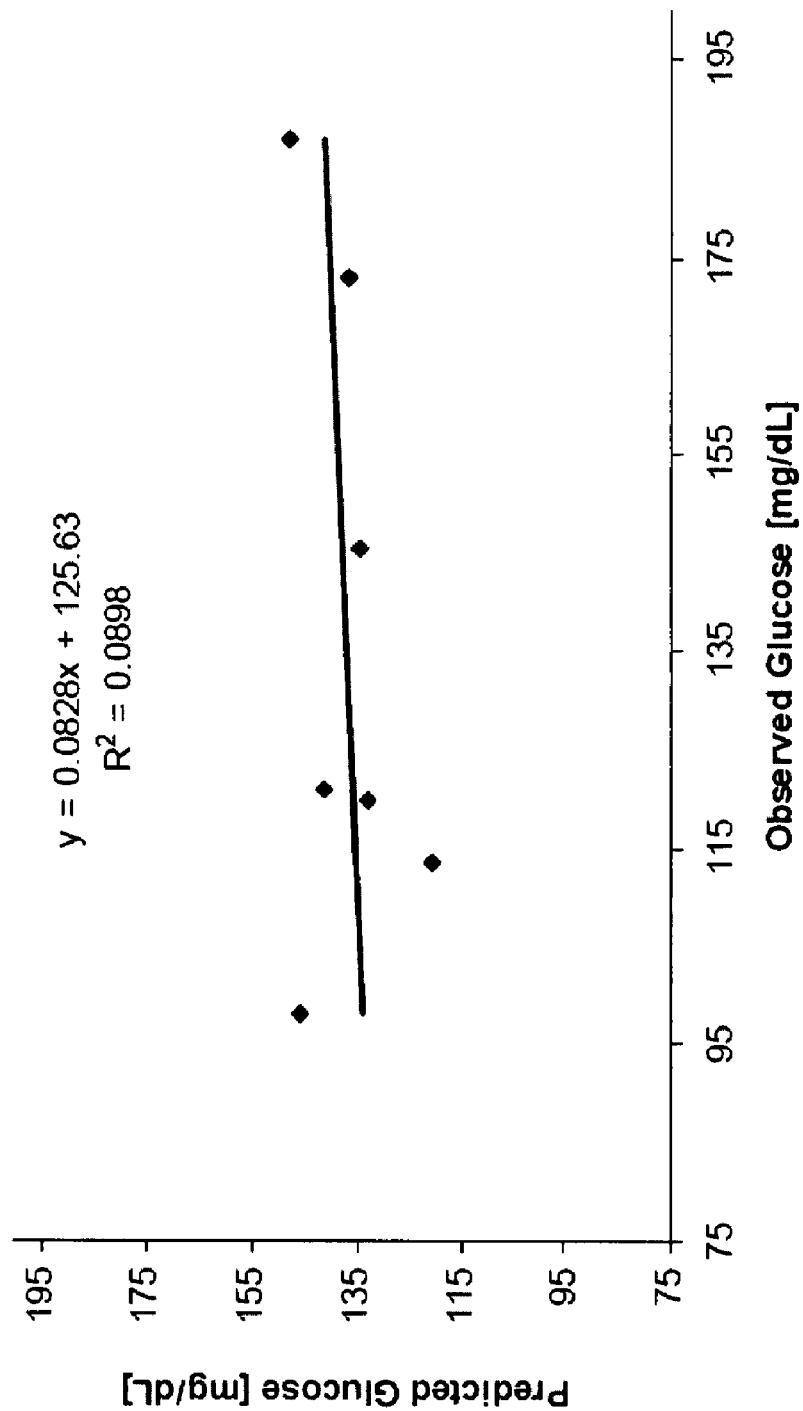
FIG. 7 provides a graph of a multiple linear regression using OAE amplitudes evoked under test conditions with no suppression.

A multiple linear regression to determine whether OAE amplitudes and latencies correlated with blood glucose levels under contralateral noise conditions was performed. A positive correlation existed for amplitudes of the nonlinear OAE residual amplitude (Pd) for both combinations of masker/probe stimulus parameters tested. FIG. 6A shows that as the subject's blood glucose level rose, so did the OAE amplitudes. FIG. 6B shows that the correlation coefficient between the suppressed OAE amplitude and glucose was 0.766. Notably, these findings conflict with those of Suckfull et al. (Acta Oto-Lanryngologica (1999) 119: 316-21) who observed an inverse correlation. High glucose levels may interfere with contralateral suppression of the OAE by the contralateral masker. The amplitude of the suppressed OAE will be lower in amplitude than the unsuppressed OAE under the same stimulus conditions due to the contralateral efferent effect. High glucose levels appear to interfere with the suppression effect, thereby yielding a larger OAE amplitude response under higher glucose conditions as shown in FIG. 6A. The regression results using amplitudes only are shown in FIG. 6B. Correlations were also observed between latencies and blood glucose levels. Results from this study support the conclusion that the amplitudes of suppressed OAEs correlate with blood glucose levels. It is significant that a similar, significant correlation between OAE amplitudes and blood glucose was not observed in the quiet condition where no contralateral noise was used to suppress the OAE ($R^2=0.090$) as is shown in FIG. 7.

Latencies measured in the quiet condition were difficult to determine due to low OAE suppression signal-to-noise ratio. When noisy latencies were excluded from the linear regression, some correlation between the OAE latencies and blood glucose levels ($R^2=0.62$ for the first stimulus combination) was found. Glucose can have a significant effect on axonal transmission speed, which may translate into an effect on suppression of the OAE due to efferent feedback paths. Improved latency measurements were obtained using ipsilateral suppression as described hereinbelow.

EXAMPLE 3

Ipsilateral Suppression Using Forward Masking During a Glucose Tolerance Test (GTT)

Both a non-diabetic and a diabetic subject were tested to determine whether an OAE suppressed using an ipsilateral forward-masking paradigm correlates with blood glucose levels. As in the study described hereinabove, the test subjects fasted for at least 8 hours prior to the instant study. They were then given a standard GTT while the forward masked OAE was recorded over the course of 1.5 hours.

Figure 8A:
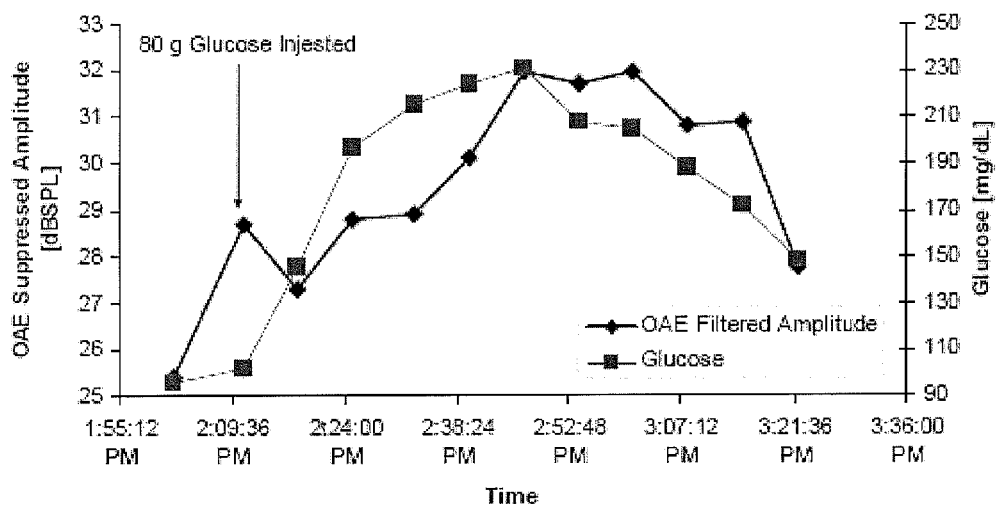
FIGS. 8A and 8B are graphs of the results from testing a non-diabetic subject using ipsilateral noise suppression during a glucose tolerance test.
Figure 8B:
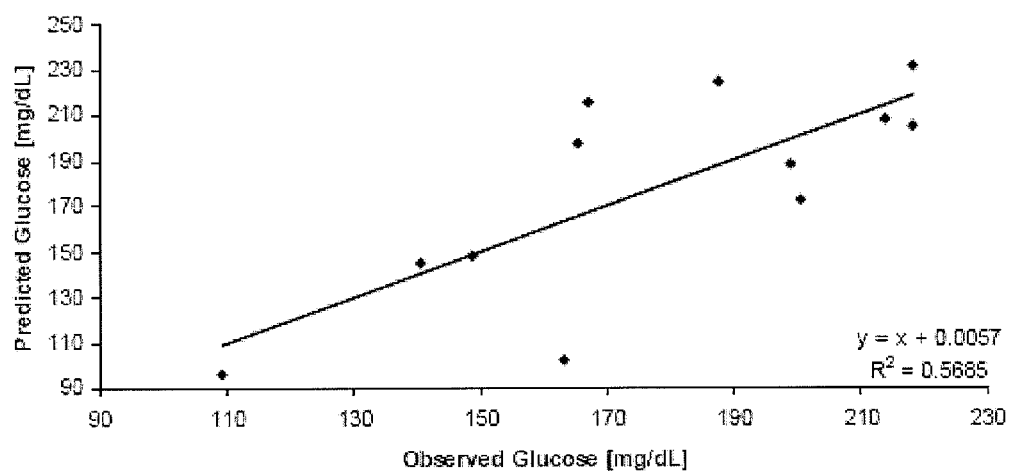

Results from the forward-masking preliminary study again demonstrated a positive correlation of the masking affect with glucose levels. FIG. 8A shows the masking effect tracking the glucose level. A linear regression was done and a correlation of 0.57 was found between the masking and the blood glucose levels (FIG. 8B). As was observed in the contralateral suppression experiments above, the suppressed OAE amplitude overall appears to increase with increasing blood glucose levels. As the blood glucose falls, the suppressed OAE amplitude also drops down again.

Figure 9A:
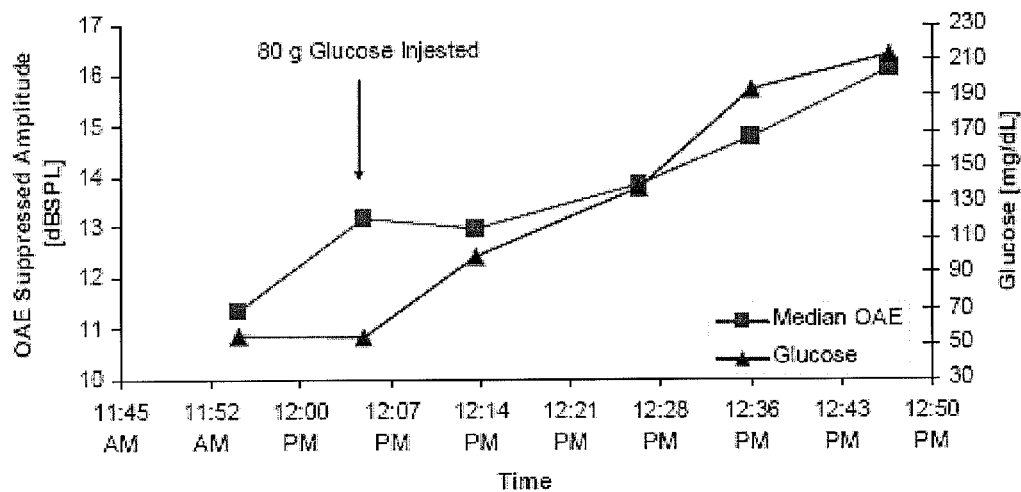
FIGS. 9A-9B are graphs of the results from testing a diabetic subject using ipsilateral noise suppression during a glucose tolerance test.
Figure 9B:
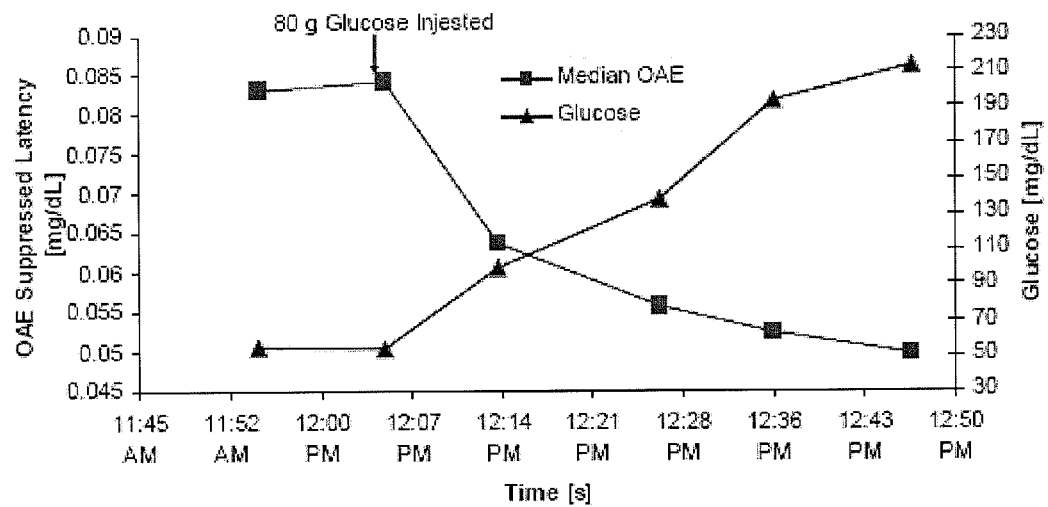
Figure 10:
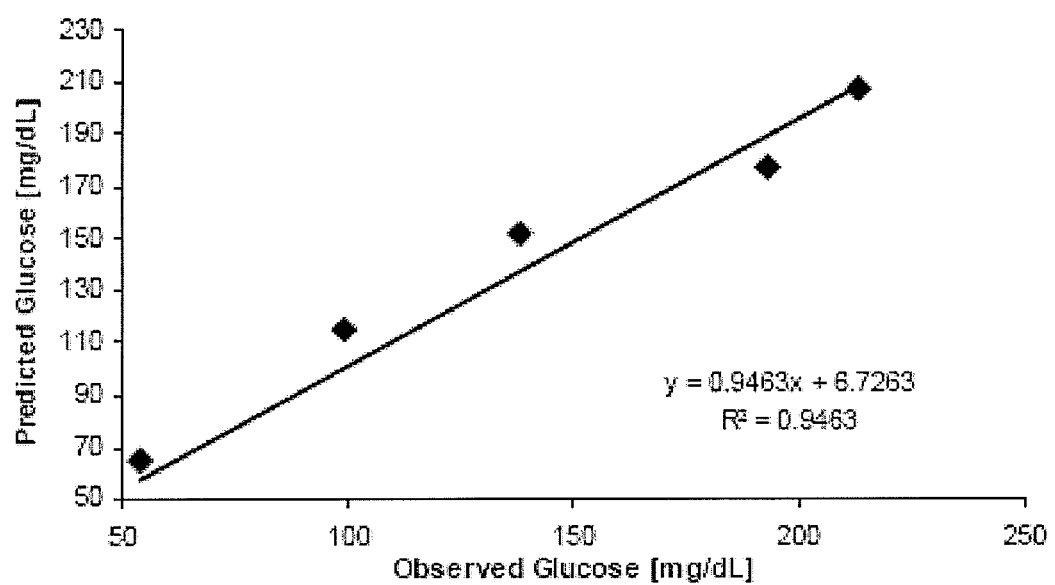
FIG. 10 is a graph showing the results from testing a diabetic subject using ipsilateral noise suppression. Amplitude and latency combined using a multiple linear regression yielded a high correlation with blood glucose ($R^2$=0.95).

The above procedure was repeated on a diabetic subject. Results were remarkable in that both the suppressed OAE amplitude and latency were observed to tightly correlate with the subject's blood glucose during the glucose tolerance test (FIGS. 9A-9B). While both amplitude and latency showed strong correlation, latency was particularly strong ($R^2=0.89$). When both latency and amplitude OAE measures were combined using multiple linear regression, the correlation was very high ($R^2=0.95$; see FIG. 10).

Notably, the subject's glucose does not return to baseline. This is because the subject did not take insulin at any point during the GTT. In practice, diabetic subjects will take an insulin shot after their glucose levels have risen high enough and the OAE can be used to monitor the subsequent fall in glucose. These experiments indicate that amplitude and latency measures of a suppressed OAE in diabetic subjects correlate with blood glucose levels.

EXAMPLE 4

Type 2 Diabetic Five-Patient GTT Study Using a Forward-Masker

Five type 2 diabetic patients were tested using a similar forward-masker stimulus paradigm described hereinabove. More specifically, the subjects underwent a glucose tolerance test (GTT) while forward-masked OAEs were evoked from the ipsilateral ear. There were three primary differences between the OAE stimulus used here as compared with the study above: 1) broadband noise was used as the masking signal; 2) the probe signal consisted of two frequencies (a 74 dB SPL 1500 Hz and an 89 dB SPL 250 Hz tone); and 3) a Ridge regression model was used to predict glucose using leave-one-out cross-validation.

Broadband noise potentially activates a more robust masking effect than narrow-band noise (Guinan, J J (2006), Ear & Hearing, 27:589-607). Further, the two-tone probe was used rather than a single-tone probe in an effort to determine whether the efferent response was due to the medial olivocochlear (MOC) reflex or the middle ear muscle (MEM) reflex. Goodman and Keefe (J. Assoc. Res. Otolaryngo. (2006) 10, 7(2):125-139) showed that a higher amplitude 250 Hz tone will be suppressed primarily by a MEM reflex while a lower amplitude 1500 Hz tone will be suppressed primarily by the MOC reflex. By observing the suppressed OAE response at these two frequencies, it could then be determined if one or the other of these reflexes had been activated by the broadband noise masker. Since both reflexes generate an efferent feedback response to the basilar membrane, it was expected that both suppression effects would correlate with glucose levels.

A Ridge regression algorithm (Tikhonov, A. N. (1943) Dokl. Akad. Nauk SSSR, 39:195-198) was used to predict glucose in this study because it was found that it generalizes better than linear regression when a small number of data points are used within the model. The method of leave-one-out cross validation (LOOCV) is a standard method for evaluating a mathematical model. In LOOCV, the ridge regression model components were derived using all data points in a sample except one. The model was then used to predict the glucose value for that one data point that was left out. Error between the actual and predicted glucose for the left-out data point was then evaluated. This procedure was used to estimate glucose for each of the data points acquired during the study.

Figure 11A:
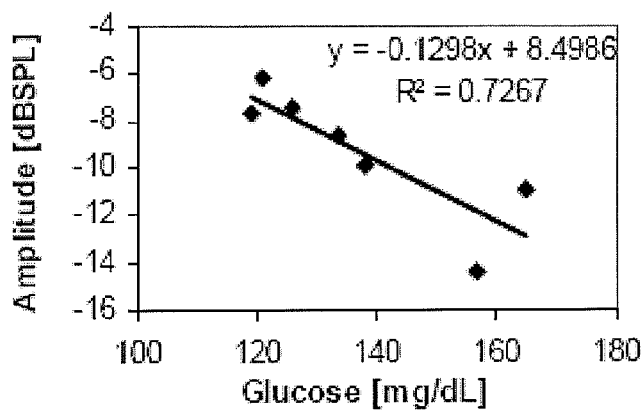
FIGS. 11A-11C are graphs of the amplitude (FIG. 11A), latency (FIG. 11B), and signal-to-noise ratio (FIG. 11C) suppression of 250 Hz probe versus glucose for a diabetic patient. All 3 metrics are inversely correlated with glucose.
Figure 11B:
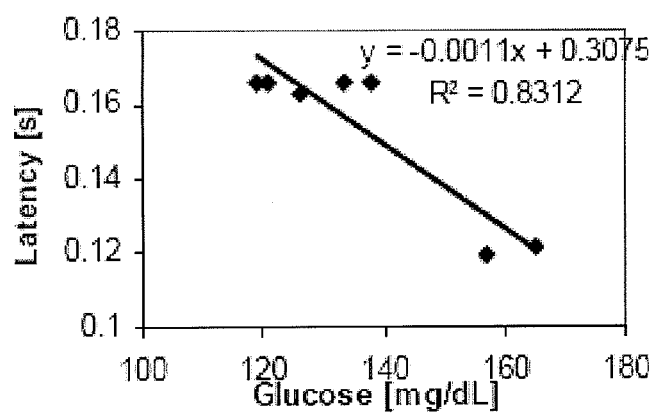
Figure 11C:
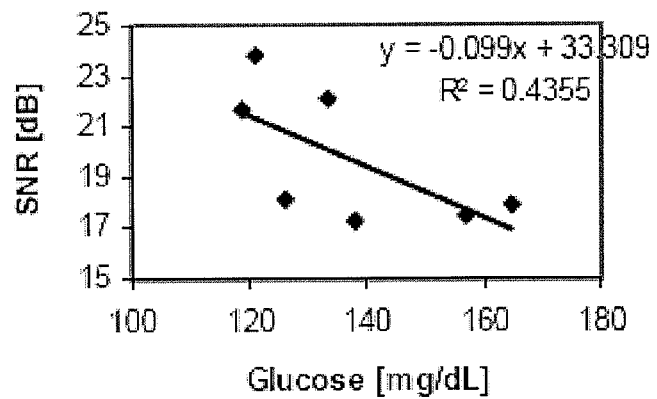

Results from this study confirm the results described hereinabove. Correlations between glucose and the OAE metrics (amplitude, latency, and SNR) were observed across all five patients. Use of the combined 250 Hz+1500 Hz probe tone confirmed the belief that the MEM reflex was being activated by the large amplitude noise and probe signals. While there was inter-subject variability in the amount of correlations observed for individual metrics, both the 250 Hz and 1500 Hz filtered suppressed OAE responses indicated a correlation with blood glucose levels across all metrics. Results from one of the patients are shown below in FIG. 11A-11C.

Figures 12A, 12B:
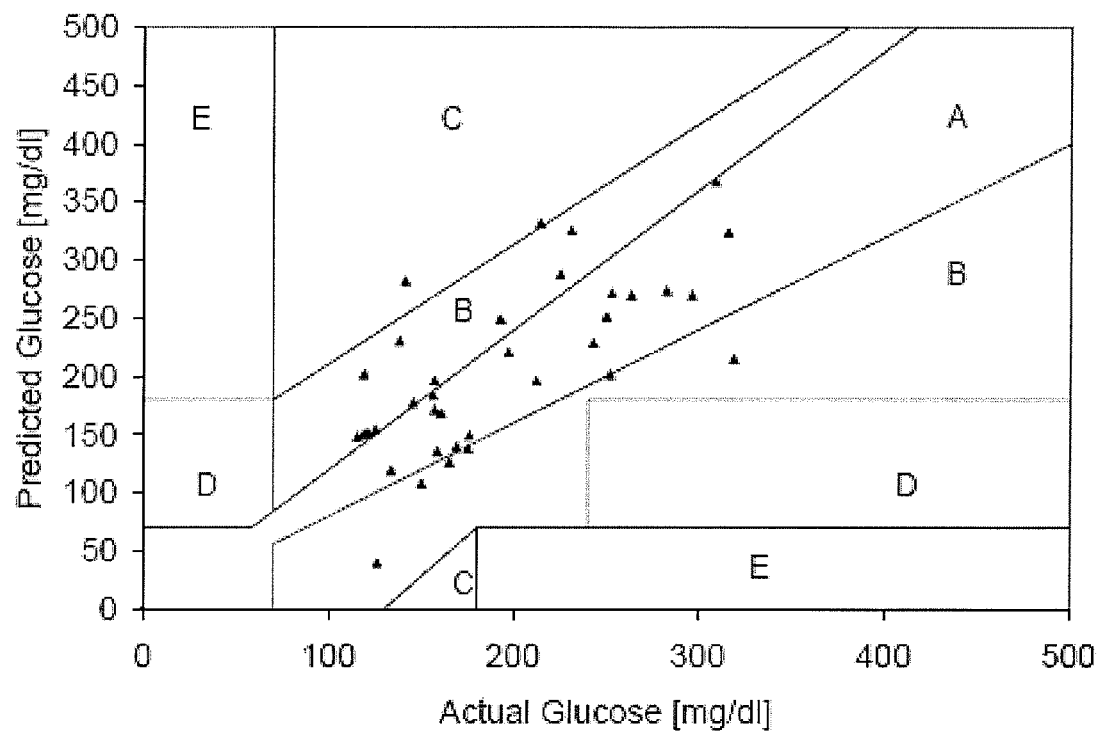
FIG. 12A is a Clarke Error Grid of the results for all five type 2 diabetic test subjects. Predicted glucose values were generated using a ridge regression algorithm following a leave one out cross-validation protocol. All predicted glucose values fall within the A, B, and C region with no points falling within the clinically unacceptable regions of D and E.
FIG. 12B is a table summarizing the data presented in FIG. 12A.

The ridge regression prediction algorithm proved to be a reasonable choice for predicting glucose levels based on the 3 dependent variables of amplitude, latency and SNR. The group results are shown as a Clarke Error Grid in FIGS. 12A-12B. From the table in FIG. 12B, it is clear that 94.6% of the predicted glucose data falls within the A and B regions while no data falls within the clinically unacceptable regions of D and E.

In summary, the above experiments have demonstrated the effectiveness of using suppressed OAEs to predict blood glucose levels, particularly in diabetic subjects. Both ipsilateral and contralateral suppression have been shown to generate a suppression effect that correlates with blood glucose levels. Accordingly, it is evident that the suppressed OAE response may be used to determine blood glucose levels, such as in diabetic subjects. While the parameters used for evoking and measuring OAEs using both ipsilateral and contralateral suppression simultaneously were effective, other parameters may also yield a usable correlation with blood glucose levels.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A system for determining a concentration of at least one analyte in a subject comprising:
    a) means for producing and recording at least one pressure signal;
    b) means for producing an audio signal to the ear of said subject, wherein application of the audio signal evokes a measured pressure signal in the ear of said patient; and
    c) at least one computing device to handle data acquisition, wherein said computing device comprises means for converting measured pressure signal information to an output of the concentration of said at least one analyte in said subject.

2. The system of claim 1 which is contained within a hand-held device or headphones.

3. The system of claim 1, wherein said means for converting the measured pressure signal comprises applying an algorithm correlating a characteristic of said measured pressure signal with said analyte concentration.

4. The system of claim 1 further comprising means for amplifying the pressure stimuli.

5. The system of claim 1 further comprising means for filtering the pressure stimuli.

6. The system of claim 1 further comprising a visual display for displaying the concentration of the at least one analyte.

7. The system of claim 1 further comprising a means for providing a physical print out of the concentration of the at least one analyte.

8. The system of claim 1 further comprising a means of transmitting the concentration of the at least one analyte to a computer.

9. A method for determining the concentration of at least one analyte in a patient comprising:
   a) evoking a measured pressure signal in the ear of said patient by applying an audio signal to said ear;
   b) measuring at least one characteristic of said measured pressure signal; and
   c) applying an algorithm correlating said characteristic of said measured pressure signal with said analyte concentration to the measured characteristic of step b), thereby determining said concentration of at least one analyte in said patient.

10. The method of claim 9, wherein said analyte is associated with a disease or disorder.

11. The method of claim 10, wherein said analyte is glucose.

12. The method of claim 9, wherein said measured pressure signal is an otoacoustic emission (OAE).

13. The method of claim 9, wherein said measured pressure signal represents a measure of the middle ear muscle reflex.

14. The method of claim 9, wherein said audio signal consists of at least one waveform selected from the group consisting of a constant, stepped, ramped, periodic, tone, chirp, click and noise.

15. The method of claim 9, wherein said measured pressure signal is masked by at least one stimulus pressure signal selected from the group consisting of a constant, stepped, ramped, periodic, tone, chirp, click and noise.

16. The method of claim 15, wherein said masking stimulus pressure signal is provided contralaterally, ipsilaterally, or both.

17. The method of claim 15, wherein said masked measured pressure signal represents a measure of at least one of the reflexes selected from the group consisting of the medial olivococlear reflex, the lateral olivocochlear reflex, and the middle ear muscle reflex.

18. The method of claim 9, wherein said characteristic of said measured pressure signal is selected from the group consisting of amplitude, latency, signal-to-noise ratio, rise time, fall time, frequency, phase, and duration.

19. The method of claim 9, wherein step c) comprises using a computing device having means for converting measured pressure signal information to an output of the concentration of said at least one analyte in said subject.

* * * * *